(12) United States Patent
Collins et al.

(10) Patent No.: US 6,706,855 B1
(45) Date of Patent: Mar. 16, 2004

(54) ANTIMICROBIAL POLYMER

(75) Inventors: Andrew Neale Collins, Manchester (GB); Brian David Bothwell, Manchester (GB); Graham John McPherson, Manchester (GB)

(73) Assignee: Avecia Limited, Manchester (GB)

( * ) Notice: Subject to any disclaimer, the term of this patent is extended or adjusted under 35 U.S.C. 154(b) by 40 days.

(21) Appl. No.: 10/070,152

(22) PCT Filed: Jul. 25, 2000

(86) PCT No.: PCT/GB00/02864

§ 371 (c)(1),
(2), (4) Date: Mar. 4, 2002

(87) PCT Pub. No.: WO01/17356

PCT Pub. Date: Mar. 15, 2001

(30) Foreign Application Priority Data

Sep. 3, 1999 (GB) ................................. 9920774

(51) Int. Cl.$^7$ .......................... C08G 73/00; C08G 73/06
(52) U.S. Cl. ....................... 528/422; 528/423; 528/425; 528/272; 528/288; 428/690; 428/917
(58) Field of Search .................................. 528/422, 423, 528/425, 272, 288; 428/690, 917

(56) References Cited

U.S. PATENT DOCUMENTS

| 5,235,045 A | 8/1993 | Lewis et al. |
| 5,498,547 A | 3/1996 | Blake et al. |

FOREIGN PATENT DOCUMENTS

| JP | 56 167383 A | 12/1981 |
| SU | 619 489 A | 7/1978 |
| WO | WO 94/09357 | 4/1994 |
| WO | WO 94/09360 | 4/1994 |
| WO | WO 98/02492 | 1/1998 |

OTHER PUBLICATIONS

S.C. Chang et al., Bioorg. Med. Chem. Lett. (1993) vol. 3, No. 4, pp. 555–556.

*Primary Examiner*—Duc Truong
(74) *Attorney, Agent, or Firm*—Pillsbury Winthrop LLP

(57) ABSTRACT

An antimicrobial polymer, characterised in that it carries a covalently bound chromophoric marker. The antimicrobial polymer is preferably a cationic antimicrobial polymer, especially a poly(hexamethylenebiguanide). Also claimed are compositions containing the antimicrobial polymer, a method for treating a medium using the antimicrobial polymer and a method for detecting the antimicrobial polymer in a medium.

23 Claims, No Drawings

ANTIMICROBIAL POLYMER

CROSS REFERENCE TO RELATED APPLICATIONS

This application is a national phase application based on PCT/GB00/02864, filed Jul. 25, 2000, and which further claims priority from British Application No. 9920774.8, filed Sep. 3, 1999. These applications in their entirety are incorporated herein by reference.

The present invention relates to antimicrobial polymers which carry a chromophoric marker, more particularly to cationic antimicrobial polymers carrying a covalently bound chromophoric marker and to methods for detecting the antimicrobial polymers on or in a medium.

Antimicrobial polymeric compounds are used in a wide range of media to control or eliminate micro-organisms, for example industrial media such as cooling water, metal working fluids, latices, surface coatings, and geological drilling fluids; recreational waters such as swimming pools and spas; and in personal care formulations such as soaps and cosmetics. The antimicrobial polymers are used in such media as preservatives, disinfectants, slimicides and algicides. Antimicrobial polymers, especially cationic antimicrobial polymers are particularly useful and offer a number of advantages over molecular quaternary ammonium compounds, because they are of relatively low toxicity and exhibit reduced foaming when added to a liquid medium such as water.

To prevent the proliferation of microorganisms in or on a medium containing an antimicrobial compound it is necessary to ensure that the concentration of antimicrobial compound is sufficient to give an antimicrobial effect In the medium. However, in most media, especially swimming pools, the concentration of antimicrobial compound reduces with time through a number of mechanisms, for example adsorption; chemical break down caused by interaction of the antimicrobial compound with micro-organisms or with other components present in the medium; and in the case of recirculating water systems such as swimming pools and spas by dilution when fresh water is added to the system. This can result in loss of the antimicrobial protection provided by the antimicrobial compound and the subsequent proliferation of micro-organisms.

To ensure that a medium remains protected by the antimicrobial compound it is therefore important that the concentration of antimicrobial compound in, or on, a medium can be accurately determined to ensure that sufficient concentration of the antimicrobial; compound is maintained. Antimicrobial compounds are typically used at very low concentrations, often less than 10 ppm. Therefore, the system used to measure the concentration of antimicrobial compound must be able to detect ppm levels of the compound, otherwise inaccurate readings will be obtained leading to incorrect dosage levels of the antimicrobial material.

In some applications there is a need to detect the presence of the antimicrobial compound at even lower levels. For example antimicrobial compounds are often used to protect fruit against microbial degradation during storage and transportation. However, before the fruit is sold to consumers it is necessary to wash the fruit to remove the antimicrobial compounds from the fruit. Typically the washing process is required to reduce the concentration of the antimicrobial compounds to about 1 to 10 ppb. In this application there is a need for accurate detection of the antimicrobial compound to ensure that all or substantially all of the compound has been removed during the washing process. Such detection therefore needs to be sensitive to ppb concentrations of the antimicrobial material.

However, the polymeric nature of polymeric antimicrobial compounds makes accurate determination of the concentration difficult and time consuming. This is especially true of cationic polymeric antimicrobial compounds because the cationic groups tend to associate themselves with a surface to which they are applied. To determine the concentration of the antimicrobial compound on a surface, for example on the surface of fruit, it is necessary to extract the antimicrobial compound from the surface and analyse the extract, for example using gel permeation chromatography. However, because most antimicrobial polymers comprise a mixture of polymer chains of different lengths, this procedure often gives a misleading result of the concentration because the extraction method tends to preferentially extract the shorter polymer chains.

Furthermore, polymeric antimicrobial compounds are often used in media which contain numerous other components which can interfere with the analysis method used to estimate the concentration of the polymeric antimicrobial compound. For example, in swimming pools poly (hexamethylenebiguanide) (PHMB) is commonly used as a primary sanitizer. A known calorimetric method for estimating the PHMB in the pool is based on, the interaction of PHMB with bromophenol blue or Eosin dyestuffs. However, this test also detects quaternary ammonium compounds which are often present in swimming pools and thereby gives a false measure of concentration of the PHMB.

There is therefore a need for a polymeric antimicrobial material which provides good protection against the growth of undesirable micro-organisms and which can be readily detected In or a medium to which it has been applied.

We have found that by covalently binding a chromophoric marker on, or in, an antimicrobial polymer enables the antimicrobial compounds to be detected with greater, accuracy, especially at low concentration without adversely affecting the antimicrobial properties of the polymer.

According to a first aspect of the present invention there is provided an antimicrobial polymer, characterised in that it carries a covalently bound chromophoric marker (hereinafter "The Polymer").

Preferably The Polymer is a cationic antimicrobial polymer, more preferably a poly(quaternary ammonium) compound, a polymeric guanide or especially a polymeric biguanide.

The chromophoric marker comprises a chromophoric group which absorbs and/or emits radiation at wavelengths characteristic of the chromophoric group. The wavelength of absorbtion and/or emission provides a reproducible "signature" associated with The Polymer by means of which it is possible to detect the presence of The Polymer using a suitable optical or spectroscopic detection method. This signature is preferably different from any absorption or emission bands inherent in the antimicrobial polymer which does not contain the chromophoric marker, because this enables more accurate detection of the chromophoric marker, particularly at low concentrations of The Polymer in a medium Preferably the chromophoric group has a major absorption and/or emission band in the UV, visible or near infra red range of the electromagnetic spectrum. A suitable absorption and/or emission range is from 275 to 1500 nm, preferably from 390 to 1100 nm, more preferably from 400 to 800 nm.

When the chromophoric group emits radiation, it may do so via phosphorescence or more preferably fluorescence.

Suitable chromophoric groups comprise an azo, anthraquinone, pyrroline, phthalocyanine, polymethine, aryl-carbonium, triphenodioxazine, diarylmethane, triarylmethane, anthraquinone, phthalocyanine, methine, polymethine, rhodamine, indoaniline, indophenol, stilbene, squarilium, coumarin, aminoketone, xanthene, fluorine, acridene, acridan, acridinium, quinolene, thiazole, azine, nigrosine, oxazine, thiazine, indigoid quininold, quinacridone, lactone, pyrroline, luciforyl, indacene, benzodifuranone, indolene, or an aromatic fluorescent group or a combination of such groups.

In a preferred embodiment of the present invention the chromophoric group is a fluorescent group which emits radiation in a specific fluorescence band at a wavelength which is longer than that of the absorption band. Preferably the fluorescent group has its major absorption band of in the range of from 300 to 100 nm, more preferably 390 to 1100 nm and especially from 400 to 800 nm. Preferably the fluorescence band is from 350 to 1550 nm more preferably from 400 to 800 nm, especially from 430 to 600 nm and more especially from 440 to 460 nm.

Preferred fluorescent groups have a quantum efficiency of at least 0.01, more preferably at least 0.1 and especially 0.5. The quantum efficiency of a fluorescent material is defined as the number of photons emitted by the fluorescent material at the peak wavelength of the emission band divided by the number of photons absorbed at the peak wavelength of the absorption band by the fluorescent material. A relatively higher quantum efficiency tends to produce a greater amount of fluorescence radiation, which is easier to distinguish from any interfering radiation that may be present. Fluorescent groups having relatively higher quantum efficiencies are generally easier to detect and can therefore be used in lower concentrations on the antimicrobial polymer.

Preferred fluorescent groups include phthalocyanine; methine; croconium; stilbene, for example 4-acetamido4'-isothiocyanatostilbene; coumarin, for example 7-amino-4-methylcoumarin and 7-amino-4-trifluoromethylcoumarin; acridan; acridinium; luciforyl; squarylium; indacene, for example 4,4-difluoro-4-bora-3a,4a-diaza-s-indacene; xanthene, for example Rhodamine B, Rhodamine 6G, Rhodamine 123, Fluorocein, 5-amino-Fluorocein and 5(4,6-dichlorotriazin-2-yl)amino-Fluorocein; and an aromatic fluorescent group.

When the fluorescent group is an aromatic fluorescent group in is preferably a fluorescent polynuclear aromatic group, such as a substituted naphthylene or substituted perylene, for example 1,8-napthalimide, 4-bromo-1,8-naphthalimide, 4-methoxy-1,8-naphthalimide, 1,5-naphthalene disulphonic acid, 2-amino-1,5-naphthalene disulphonic acid, 1,8-naphthalic anhydride, 4-bromo-1,8-naphthalic anhydride, 4-methoxy-1,8-naphthalic anhydride, 1,4,5,8-naphthalenetetracarboxylic acid dianhydride or perylene and imides thereof.

It is especially preferred that the fluorescent group is a 1,8-naphthalimide or 1,4,5,8-naphthalenetetracarboximide, or a derivative thereof.

In another preferred embodiment, the chromophoric group is one which produces a characteristic Raman spectrum when irradiated with monochromatic light. Preferred chromophores in this embodiment are rhodamines and azo dyes, especially Rhodamine 6G.

The chromophoric marker may be covalently bound to the antimicrobial polymer as a pendant group or a terminal group on the polymer chain or, most preferably as an in-chain group in the polymer chain.

When the chromophoric marker is present as a pendant or terminal group on the polymer chain, the covalent bond between the polymer and the marker is preferably formed by means of a reactive functional group on the chromophoric marker which is capable of forming a covalent bond with the polymer and/or monomer precursors used to make the polymer.

When the chromophoric marker is incorporated into the polymer chain the chromophoric marker preferably has a plurality, preferably two reactive functional groups which are capable of forming a covalent bond with one or more of the monomers, or chain segments, used to prepare the polymer and is thereby incorporated covalently as a component in the polymer chain.

The chromophoric marker may be incorporated into The Polymer by means of, for example, an ester, ether, amide, amine, imide, carbamate, disulphide, sulphide, sulphonamide, sulphonic acid ester, ureylene, thioureylene, carbonate or urethane group.

The reactive functional group(s) carried by the chromophoric marker may be any functionality which is capable of reacting with the antimicrobial polymer or a monomer used in the preparation of the antimicrobial polymer to form a covalent bond therewith. Preferred reactive functional groups include —OH, —NHR$^1$, —NH—, —SH, —COOR$^1$, —COZ, —SO$_2$Z, epoxy, alkenyl, isocyanate, thioisocyanate, an acid anhydride group or a halogen atom (preferably chlorine or bromine), wherein R$^1$ is H, optionally substituted alkyl or optionally substituted phenyl and Z is halogen (especially chlorine). Preferably R$^1$ is H, C$_{1-6}$-alkyl or phenyl. More preferably R$^1$ is H or C$_{1-4}$-alkyl.

More preferably the reactive functional group is —NH$_2$, —OH, —SH, —NCO, bromine, chlorine or —NCS. It is especially preferred that the reactive functional group is —NH$_2$, —NCO or —NCS, more especially —NH$_2$.

The reactive functional group(s) may be attached directly to the chromophoric group (i.e. as an integral part of the chromophoric group) or, more preferably, through a linker group.

Preferred linker groups are aliphatic (preferably alkylene or alkenylene), arylene, heteroarylene or a combination thereof. When the linker group is aliphatic it preferably contains up to 10 carbon atoms. The aliphatic group may be branched but is preferably a straight chain group. Preferably the aliphatic group is a C$_{2-6}$-alkylene or a C$_{2-10}$-alkenylene group and especially a C$_{2-6}$-alkylene group. The aliphatic group may also contain one or more hetero atoms selected from O, S and N.

When the linker group is an arylene group it is preferably naphthylene or more preferably phenylene.

When the linker group is heteroarylene it is preferably a triazinylene or pyrimidinylene group.

When the linker group is an aliphatic, arylene or heteroarylene group it may be attached to the chromophoric group directly or, more preferably by means of a divalent atom or group. Preferred divalent atoms and groups include —O—, —S—, =N—, amide, ester, a sulphonamide, carbamate, —NR$^1$—, —NR$^1$C(O)NR$^1$— or —NR$^1$C(S)NR$^1$—, wherein R$^1$ is as hereinbefore defined.

The linker group may comprise a combination of the hereinbefore mentioned atoms and groups. For example the linker may comprise an alkyleneamino group wherein the amino group is attached to the chromophoric group and the alkylene group connects the amino group and the reactive functional group. By way of an example of a chromophoric marker carrying a combination of linker groups is the compound of the formula:

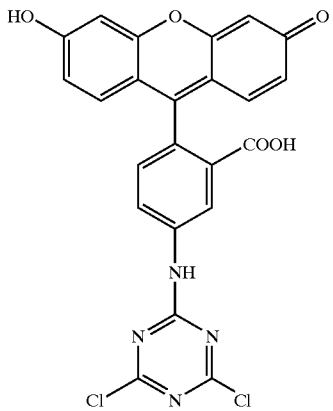

wherein the linker group comprises the triazinyl amino group and the reactive functional groups are the labile chlorine atoms on the traizine ring.

An especially preferred chromophoric marker which carries reactive functional group(s) is of the Formula (1):

Ch-{[(T)$_m$L]$_n$X}$_p$     Formula (1)

wherein:

| | |
|---|---|
| Ch | is a chromophoric group; |
| L | is a divalent aliphatic linking group; |
| X | is a reactive functional group as hereinbefore defined; |
| T | is —O—, —S—, —NR$^1$—, —NR$^1$C(O)NR$^1$—, —NR$^1$C(S)NR$^1$—, —NR$^1$C(O)—, —OC(O), =N— or —SO$_2$NR$^1$—; |
| R$^1$ | is as hereinbefore defined; |
| m and n | independently are 0 or 1; and |
| P | is 1 or 2. |

Preferably L is one of the hereinbefore mentioned aliphatic linking groups, more preferably C$_{2-8}$-alkylene and especially C$_{2-6}$-alkylene. n is preferably 1. X is preferably —OH, —NH$_2$ or —SH. m is preferably 1. T is preferably —NH—.

When the chromophoric marker is attached to the antimicrobial polymer as a terminal or pendant group, p is 1. When the chromophoric marker is attached as an in-chain group in the antimicrobial polymer, p is 2.

Preferred chromophoric groups represented by Ch are the hereinbefore defined preferred chromophoric groups.

Suitable mono functional chromophoric markers of the Formula (1) which carry a reactive functional group attached directly to the chromophore (i.e. those in which n and m in Formula (1) are both 0 and p is 1) include 4-acetamido-4'-isothiocyanatostilbene-2,2'-disulphonic acid, tetramethyl-rhodamine isothiocyanate, 1,8-naphthalic anhydride, 4-bromo-1,8-naphalthimide and N-hexyl-4-bromo-1,8-naphthalimide.

Suitable mono-functional chromophoric markers of the Formula (1) carrying a single reactive functional group attached to a chromophoric group via linking group(s) (i.e. those in which n and p are both 1 in Formula (1)) include N-(6-aminohexyl)4-methoxy-1,8-naphthalimide and groups of the formulae:

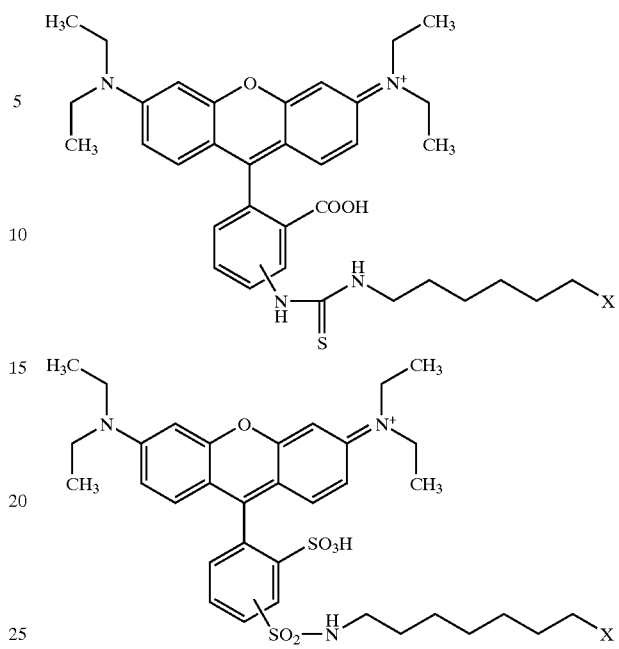

wherein X is a reactive functional group as hereinbefore defined (for example NH$_2$).

The above mentioned monofunctional chromophoric markers are suitable for use as a chain terminating or chain pendant group on the antimicrobial polymer.

Suitable bifunctional chromophoric markers of the Formula (1) carrying two reactive functional groups attached directly to a chromophoric group (i.e. those in which those in which n and m in Formula (1) are both 0 and p is 2) include 4,4'-diisothiocyanatostilbene-2,2'-disulphonic acid and 1,4,5,8-naphthalene tetracarboxylic acid dianhydride.

Suitable bifunctional chromophoric markers of the Formula (1) carrying two reactive functional groups attached to a chromophoric group via linking group(s) (i.e. those in which n is 1 and p is 2 in Formula (1)) include N-(6-aminohexyl)-4-(6-aminohexylamino)-1,8-naphthalimide and N-(6-aminohexyl)-4-methoxy-1,8-naphthalimide.

The chromophoric markers of Formula (1) may be prepared using conventional techniques, for example by condensing a compound of the formula Ch-W with the compound of the formula H-{[(T)$_m$L]$_n$X}$_p$, wherein W is a suitable leaving group (for example Cl) and Ch, T, L, X, m, n and p are as hereinbefore defined. Under some circumstances it may be necessary to use a suitable protecting group on the reactive functional group X to prevent it reacting with the compound Ch-W. For example, the reaction may be performed using a suitable polymer support such as a Wang resin to which the reactive group X is bound during reaction with the compound Ch-W. Following the reaction the bond with the Wang resin is cleaved, using a suitable reagent, for example an acid such as trifluoroacetic acid.

Especially preferred chromophoric markers of the Formula (1) are of the Formula (2):

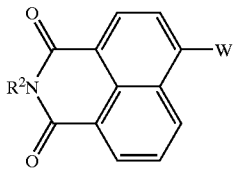

Formula (2)

wherein:
W is —NR$^3$R$^4$, —OR$^5$ or halogen;
R$^2$, R$^3$ and R$^5$ are each independently, alkyl optionally substituted by a reactive functional group;
R$^4$ is H or alkyl optionally substituted by a reactive functional group;
provided that at least one of R$^2$ R$^3$, R$^4$ or R$^5$ is substituted by a reactive functional group.

When W is halogen it is preferably chloro or more preferably bromo. It is preferred however that W is —OR$^5$ or —NR$^3$R$^4$.

R$^2$ and R$^3$ are preferably C$_{1-10}$alkyl, more preferably C$_{1-6}$-alkyl, especially C$_{2-6}$-alkyl and more especially hexyl substituted by a reactive functional group.

Preferably R$^5$ is C$_{1-6}$-alkyl, more preferably C$_{1-4}$-alkyl optionally substituted by a reactive functional group. It is especially preferred that R$^5$ is methyl or ethyl.

Preferred reactive functional groups which may be present on any of R$^2$, R$^3$ R$^4$ or R$^5$ are the reactive functional groups represented by X as hereinbefore defined, more preferably —NH$_2$, —SH, —NCO or —NCS and especially —NH$_2$.

R$^4$ is preferably H or C$_{1-6}$-alkyl optionally substituted by amino, hydroxy or mercapto. It is especially preferred that R$^4$ is H.

Especially preferred compounds of the Formula (2) include N-(6-aminohexyl)-4-(6-aminohexylamino)-1,8-naphthalimide (alternatively 2-(6-aminohexyl)-6-(6-aminohexylamino)-benzo[de]isoquinoline-1,3-dione), N-(6-aminohexyl)-4-methoxy-1,8-naphalthimide, N-(6-aminohexyl)-4-bromo-1,8-naphalthimide and N-hexyl-4-(6-aminohexyl)-1,8-naphthalimide.

The compounds of Formula (2) are novel and form a further aspect of the present invention.

The compounds of Formula (2) may be prepared by reacting a 4halo-1,8-naphthalic anhydride with 1 molar equivalent of a compound of the formula NH$_2$R$^2$. The reaction is preferably performed under anhydrous conditions. Optionally the reaction may be performed in a suitable inert solvent such as an ether, for example tetrahdrofuran or an alcohol, for example ethanol. The reaction is preferably performed at a temperature of from 30 to 100° C. If R$^2$ carries a reactive functional group it may be desirable to use a suitable protecting group or solid support to prevent the reactive functional group from reacting with the naphthalic anhydride.

When W is —OR$^6$ or —NR$^3$R$^4$ the product of the reaction with the naphthalic anhydride is condensed with approximately 1 molar equivalent of a compound of the formula WH. Alternatively, when W is —OR$^5$ the product of the reaction with the naphthalic anhydride may be reacted with the corresponding alkoxide of the formula MOR$^2$, wherein M is an alkali metal such as sodium.

In another embodiment of the present invention the chromophoric marker is of the Formula (A):

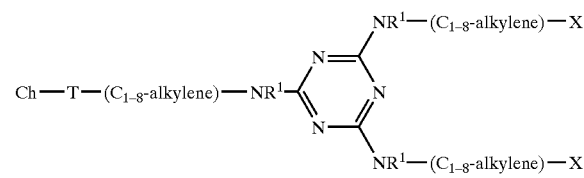

Formula (A)

wherein:
Ch, T, each R$^1$ and each X$^1$ are, independently, as hereinbefore defined.

The chromophoric markers of Formula (A) may be prepared using conventional methods used in the preparation of dyes. For example a suitable technique comprises condensing the compound of the formula:

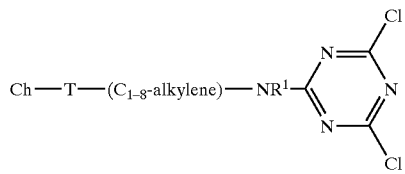

with approximately two molar equivalents of the compound of the formula:

NHR$^1$—(C$_{1-6}$-alkylene-$_x$ wherein Ch, R$^1$,Y$^1$ and X$^1$ are as hereinbefore defined. Where appropriate the reactive functional group may be protected during the reaction as hereinbefore described for example by using a solid support such as a Wang resin. Preferred chromophoric markers of the Formula (A) are of the formulae:

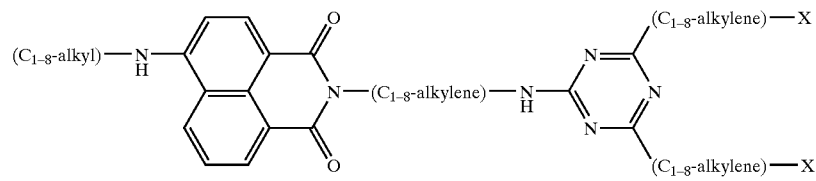

-continued

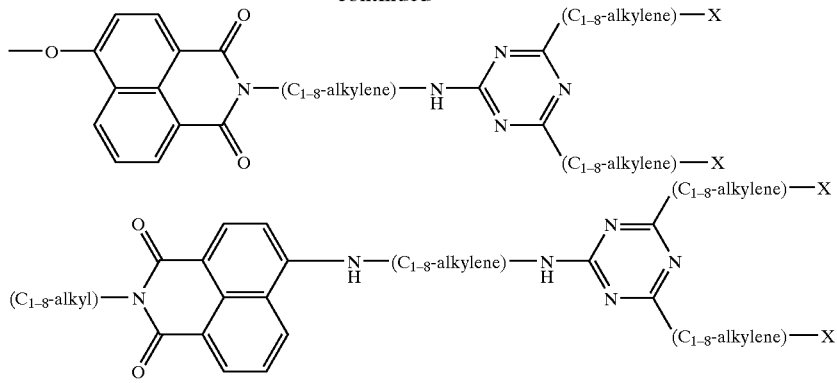

wherein X is as hereinbefore defined.

Preferably the chromophoric marker is present in The Polymer at a concentration which is insufficient to significantly affect the antimicrobial properties of the polymeric material compared to a polymer without the chromophoric marker. Preferably the chromophoric marker is present at less than 10%, more preferably less than 5%, especially less than 1% based upon the total weight of The Polymer. It is especially preferred that the chromophoric marker is present at approximately 0.1% based upon the total weight of The Polymer.

As hereinbefore mentioned the chromophoric marker is covalently bound to the antimicrobial polymer. The covalent bond is preferably formed by means of reaction of one of the herein described reactive functional group with a suitable atom or group present in the antimicrobial polymer or the monomer(s) used to prepare the antimicrobial polymer. The choice of reactive functional group will depend upon the nature of the antimicrobial polymer to which it will be bound. For example, when the chromophoric marker is bound to the polymer by means of an ester group, the ester may be formed by reaction of a carboxylic acid group present on the chromophoric marker with a pendant hydroxy group on the antimicrobial polymer, or vice versa.

When the chromophoric marker carries an acid anhydride group, the chromophoric marker is conveniently bound to the antimicrobial polymer by means of an imide group formed by reaction of an amine group on the polymer with the acid anhydride group.

The antimicrobial polymer to which the chromophoric marker bound may be any antimicrobial polymer, preferably a cationic antimicrobial polymer, more preferably an antimicrobial poly(quaternary ammonium) compound or a polymeric guanide and especially a polymeric biguanide.

Preferred antimicrobial poly(quaternary ammonium) compounds to which the chromophoric group is covalently bound include, for example, the Ionene polymers described in U.S. Pat. No. 5,866,016 cols 6 to col. 9 which are incorporated herein by reference thereto, especially poly [oxyethylene(dimethyliminio)ethylene(dimethyliminio) ethylene dichloride] (commercially available as WSCP™ from Buckman Laboratories Inc.), poly[hydroxyethylene (dimethyliminio)ethylene(dimethyliminio)methylene dichloride] and a copolymer obtainable by copolymerising 1,2-ethylenediamine, (chloromethyl)oxirane and N-methyl amine (commercially available as Busan 1157 from Buckman Laboratories Inc.).

When the chromophoric marker is attached as a pendant or terminal group on a polymeric biguanide, the polymeric biguanide to which it covalently bound contains at least one biguanide unit of Formula (3):

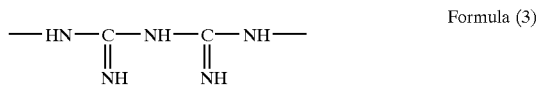

Formula (3)

Preferably, the polymeric biguanide contains at least two biguanide units' of Formula (3) which are linked by a bridging group which contains at least one methylene group. The bridging group may include a polymethylene chain which may optionally be interrupted by hetero atoms such as oxygen, sulphur or nitrogen. The bridging group may include one or more cyclic nuclei which may be saturated or unsaturated. Preferably, the bridging group is such that there are at least three, and especially at least four, carbon atoms directly interposed between two adjacent biguanide units of Formula (3). Preferably, there are not greater than ten and especially not greater than eight carbon atoms interposed between two adjacent biguanide units of Formula (3).

The polymeric biguanide may be terminated by any suitable group which may be a hydrocarbyl or substituted hydrocarbyl group or an amine or a group.

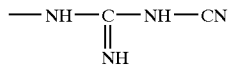

When the terminating group is a hydrocarbyl group, it may be alkyl, cycloalkyl or aralkyl.

When the terminating group is a substituted hydrocarbyl group, the substituent may be any substituent that does not exhibit an undesirable adverse effect on the micro-biological properties of the polymeric biguanide. Examples of such substituents or substituted hydrocarbyl groups are aryloxy, alkoxy, acyl, acyloxy, halogen and nitrile.

The polymeric biguanide preferably contains more than two biguanide units of Formula (3) and preferably is a linear polymeric biguanide which has a recurring polymeric unit represented by Formula (4):

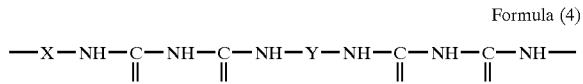

Formula (4)

wherein X and Y may be the same or different and represent bridging groups in which, together, the total number of carbon atoms directly interposed between the pairs of nitrogen atoms linked by X and Y is not less than 9 and not greater than 17.

The bridging groups X and Y may consist of a polymethylene chain, optionally interrupted by a heteroatom such as oxygen, sulphur or nitrogen. X and Y may also incorporate a cyclic nucleus which may be saturated or unsaturated, wherein the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

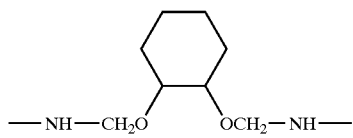

is 4 and not 8.

The preferred polymeric biguanide for use in the present invention is poly(hexamethylenebiguanide), in which both X and Y in Formula 4 are the group —(CH$_2$)$_6$—

The polymeric biguanides of Formula 4 are typically obtained as mixtures of polymers in which the polymer chains are of different lengths. Preferably, the number of individual biguanide units

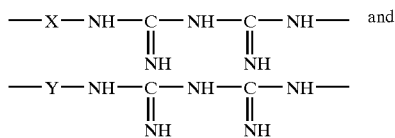

is, together, from 3 to about 80.

In the case of the preferred poly(hexamethylenebiguanide) it is a mixture of poly(hexamethylenebiguanide) polymer chains in which the individual polymer chains, excluding the terminal groups, are represented by Formula (5) and salts thereof:

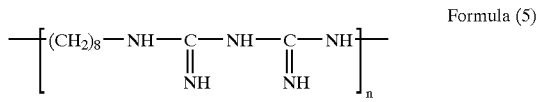

Formula (5)

wherein the value of n is from 4 to 40 and especially from 4 to 15. It is particularly preferred that the average value of n in the mixture is 12. Preferably, the average molecular weight of the polymer mixture is from 1100 to 3300.

When the chromophoric marker is present as an in-chain group in The Polymer, The Polymer is obtainable by co-polymerising the chromophoric marker with the monomers used to prepare the antimicrobial polymer which does not contain the chromophoric marker. For example, a polymeric quaternary ammonium antimicrobial material obtainable by co-polymerising 1,2-ethlenediamine, (chloromethyl) oxirane, N-methyl amine and a chromophoric marker as hereinbefore defined.

In a preferred embodiment of the present invention The Polymer is a polymeric biguanide wherein the chromophoric marker is incorporated into the polymer chain. In this preferred embodiment The Polymer is obtainable by the copolymerisation Of a chromophoric marker, a bisdicyandiamide having the formula:

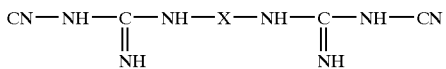

and a diamine H$_2$N—Y—NH$_2$, wherein X and Y have the meanings defined above. Alternatively The Polymer is obtainable by copolymerisation of a chromophoric marker, a diamine salt or dicyanimide having the formula:

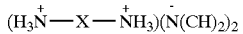

and a damine H$_2$N—Y—NH$_2$ wherein X and Y have the meanings defined above. These methods of preparation are analogous to those described in UK specifications numbers 702,268 and 1,152,243 respectively. Any of the polymeric biguanides described in GB 702,268 and GB 1,152,243 may be prepared with a chromophoric marker present in the polymer chain by addition of a chromophoric marker during the copolymerisaton of the monomers used to prepare the polymeric biguanides described therein.

It is especially preferred that The Polymer is obtainable by co-polymerising hexamethylenediamine, hexamethylene-1,6-bis dicyandiamide (HMBDA) and a chromophoric marker.

In this preferred embodiment the chromophoric marker is preferably a compound of the Formula (2) as hereinbefore defined. It is especially preferred that the chromophoric marker of the Formula (2) is N-(6-aminohexyl)-4-(6-aminohexylamino)-1,8-naphthalimide, N-(6-aminohexyl)-4-methoxy-1,8-naphthalimide, N-(6-aminohexyl)-4-bromo-1,8-naphthalimide or N-hexyl-4-(6-aminohexyl)-1,8-naphthalimide. We have found that these chromophoric marker provide a strong fluorescent signal and the presence of the aminohexyl groups closely resemble the hexamethylene groups present in the unmarked poly(hexamethylenebiguanide) polymer, thereby minimising the effect of the chromophoric marker on the antimicrobial properties of The Polymer compared to the unmarked antimicrobial polymer.

In another preferred embodiment The Polymer is obtainable by co-polymerising hexamethylenediamine, hexamethylene-1,6-bis dicyandiamide (HMBDA) and a 4halo-1,8-naphthalic anhydride, especially 4-bromo-1,8-naphthalic anhydride.

It is believed that during the copolymerisation the 4-bromo-1,8-naphthoalic anhydride reacts with 2 molar equivalents of the hexamethylene diamine to give N-(6-aminohexyl)-4-(6-aminohexylamino)-1,8-naphthalimide. The 1,8-naphthalimide groups are thereby incorporated into The Polymer as an in-chain chromophoric marker. This preferred embodiment has the advantage that it enables simple incorporation of the chromophoric marker into the antimicrobial polymer without the need for additional process stages to functionalise the naphthalic anhydride with alternative reactive functional groups (such as aminohexyl groups) prior to reaction with the monomers.

In these preferred embodiments the co-polymerisation of the hexamethylenediamine, hexamethylene-1,6-bis dicyandiamide (HMBDA) and a chromophoric marker containing reactive functional groups is preferably performed at a temperature of from 80 to 200° C., more preferably 110 to 170° C. and especially from 120 to 160° C. The molar ratio of HMBDA to hexamethylenediamine is preferably approximately 1:1

When The Polymer is cationic, it may be used in free base form but is preferably used in the form of a salt with an acid. Preferred salts are those with an inorganic acid, especially the hydrochloride salt, and salts with organic acids. Preferred salts with organic acids are those with organic carboxylic acids, preferably carboxylic acid with from 1 to 20, more preferably from 4 to 20 carbon atoms (excluding the carbon of the carboxyl group) and optionally one or more hydroxy substituent, for example acetate, stearate or gluconate salt.

In an embodiment of the present invention The Polymer is present in admixture with one or more antimicrobial polymers which do not contain a chromophoric marker. The Polymer may be, apart from the marker, different from the antimicrobial polymer which does not contain the chromophobic marker, but is preferably the same. Such mixture may arise during manufacture wherein the amount of the chromophoric maker relative to the antimicrobial polymer, or precursor chain segments or monomers, is less than that required to give a mixture of antimicrobial polymers wherein each polymer contains one or more chromophoric markers. Alternatively, the mixture of polymers may arise from mixing together The Polymer and an antimicrobial polymer which does not contain the antimicrobial marker. In this instance The Polymer constitutes a master batch concentrate. The amount of the chromophoric marker to antimicrobial polymer may, therefore, vary over wide limits. At one extreme, the mixture of antimicrobial polymers contains sufficient polymers containing the chromophoric marker to allow for detection of the mixture at the ppb level and at the other extreme the mixture of polymers contains only polymers which contain the chromophoric marker group.

According to a further aspect of the invention there is provided a composition comprising antimicrobial polymers at least some of which contain a chromophoric marker.

Preferably, in this embodiment, the amount of the chromophoric marker is not greater than 10%, more preferably not greater than 1%, even more preferably not greater than 0.01% and especially not greater than 0.001%, by weight, based on the amount of antimicrobial polymers.

According to a second aspect of the present invention there is provided a composition comprising a carrier and The Polymer.

The carrier may be a solid but is preferably a liquid.

The liquid may be water, a polar organic solvent or a mixture thereof.

When the carrier is water, the aqueous composition may also contain other adjuvants which help distribute The Polymer uniformly throughout the composition. Examples of such adjuvants are compounds which provide structure to the water to inhibit sedimentation such as alginates and gums, particularly Xanthan gum.

By the term "polar" in relation to the organic solvent is meant an organic liquid or resin capable of forming moderate to strong bonds as described in the article entitled "A Three Dimensional Approach to Solubility" by Crowley et al in Journal of Paint Technology, Vol. 38, 1966, at page 269. Such organic liquids generally have a hydrogen bonding number of 5 or more as defined in the above mentioned article.

Examples of suitable polar organic liquids are amines, ethers, especially lower alkyl ethers, organic acids, esters, ketones, glycols, alcohols and amides. Numerous specific examples of such moderately strongly hydrogen bonding liquids are given in the book entitled "Compatibility and Solubility" by Ibert Mellan (published in 1968 by Noyes Development Corporation) in Table 2.14 on pages 39–40 and these liquids all fall within the scope of the term polar organic liquid as used herein.

The Polymer and compositions according to the present invention may be used to protect various media from microbiological growth.

According to a third aspect of the invention there is provided a method for inhibiting microbiological growth on, or in a medium which comprises treating the medium with The Polymer. The Polymer can be used in any conditions in which microorganisms grow and cause problems. Thus, the medium may be an industrial medium such as a cooling water tower liquid, paper mill liquor, metal working fluid, geological drilling lubricant, polymer emulsion, surface coating composition such as paint, varnish or lacquer. The medium to be protected can be a solid such as wood or leather and particularly solid surfaces in the health-care or food preparation industries. The solid may also be a textile material such as cellulose, including its blends with synthetic polymers and also non-woven materials such as those used in disposable items such as nappies, incontinence pads and feminine hygiene packs.

The Polymer and compositions thereof according to the invention may also be used in personal care formulations which are of many types and include water-in-oil and oil-in-water emulsions. Many of these personal care formulations involve applications to the skin and include, inter alia, hand lotions, foundation creams, emollient creams, facial washing creams, shaving creams, after-shave lotions, sunscreen lotions and creams, sunscreen hair protectors, after-sun lotions, antiperspirants, deodorants, hair gels, hair colorants, hair mousse, mascara, eye shadows, eye liners, lipstick, lip gloss, facial blusher, rouge, foundations and fragrances, shampoo, shampoo gel, conditioning rinse, toothpaste, mouthwash, foam bath liquid, soluble bath oil and liquid soap formulations.

Where the medium to be protected is a solid, The Polymer may be applied by any method known to the art such as spraying, dipping or coating with a composition containing The Polymer.

The Polymers according to the present invention are particularly suitable for use in recirculating recreational water systems such as swimming pools and spas.

As noted hereinbefore, the amount of The Polymer which is applied to the medium to be protected from microbiological growth may be just sufficient to inhibit such growth or it may be in excess of such amount. Preferably, the amount of The Polymer which is applied to such medium is not greater than 2% and more preferably not greater than 1% by weight of the medium. Generally, adequate protection is provided by from 1 ppm to 500 ppm, particularly 10 to 200 ppm and especially 10 to 100 ppm of The Polymer relating to the medium.

The Polymer according to the present invention may be used alone or in combination with one or more further antimicrobial compound so as to increase the antimicrobial spectrum of activity. When The Polymer is used with another antimicrobial compound the components of such a mixture preferably provide a synergistic increase in antimicrobial effectiveness compared with the individual antimicrobial compounds in the composition. Indeed, many of the following examples exhibit synergism with The Polymer.

Examples of antimicrobial compounds which may be used with The Polymer include one or more of quaternary ammonium compounds such as N,N-diethyl-N-dodecyl-N-benzylammonium chloride; N,N-dimethyl-N-octadecyl-N-(dimethylbenzyl)ammonium chloride; N,N-dimethyl-N,N-didecylammonium chloride; N,N-dimethyl-N,N-didodecylammonium chloride; N,N,N-trimethyl-N-tetradecylammonium chloride; N-benzyl-N,N-dimethyl-N-($C_{12}$-$C_{18}$-alkyl) ammonium chloride: N-(dichlorobenzyl)-N, -N-(dimethyl-N-dodecylammonium chloride; N-hexadecylpyridinium chloride;

N-hexadecylpyridinium bromide; N-hexadecyl-N,N,N-trimethylammonium bromide; N-dodecylpyridinium chloride; N-dodecylpyridinium bisulphate; N-benzyl-N-dodecyl-N,N-bis(beta-hydroxy-ethyl)ammonium chloride; N-dodecyl-N-benzyl-N,N-dimethylammonium chloride; N-benzyl-N,N-dimethyl-N-($C_{12}$-$C_{18}$-alkyl) ammonium chloride; N-dodecyl-N,N-dimethyl-N-ethylammonium ethylsulphate; N-dodecyl-N,N-dimethyl-N-(1-naphthylmethyl) ammonium chloride; N-hexadecyl-N,N-dimethyl-N-benzylammonium chloride; N-dodecyl-N,N-dimethyl-N-benzylammonium chloride and 1-(3-chloroally)-3,5,7-triaza-1-azonia-adamantane chloride; urea derivatives such as 1,3-bis(hydroxymethyl)-5,5-dimethylhydantoin; bis (hydroxymethyl)urea; 3-(3,4-dichlorophenyl)1,1-dimethylurea; 3-(4-isopropylphenyl)-1,1-dimethylurea; tetrakis (hydroxymethyl)acetylene diurea; 1-(hydroxymethyl)-5,5-dimethylhydantion and imidazolidinylurea; amino compounds such as 1,3-bis(2-ethyl-hexyl)-5-methyl-5-aminohexahydro-pyrimidine; hexamethylenetetramine; 1,3-bis(4-aminophenoxy)propane; and 2-[(hydroxymethyl)-amino]ethanol; imidazole derivatives such as 1[2-(2,4-dichloro-phenyl)-2-(2-propenyloxy)ethyl]-1H-imidazole; 2-(methoxycarbonyl-amino)-benzimidazole; nitrile compounds such as 2-bromo-2-bromomethylglutaronitrile, 2-chloro-2-chloro-methylglutaro-nitrile; 2,4,5,6-tetra-chloroisophthaladinitrile; thiocyanate derivatives such as methylene(bis)thiocyanate; tin compounds or complexes such as tributyltinoxide, chloride, naphthoate, benzoate or 2-hydroxybenzoate; isothiazolin-3-ones such as 4,5-trimethylene-4-isothiazolin-3one, 2-methyl-4,5-trimethylene-4-isothiazolin-3one, 2-methylisothiazolin-3-one, 5-chloro-2-methyl-isothazolin-3-one, benzisothiazolin-3-one; 2-n-butylbenzisothiazolin-3-one; 2-n-hexylbenzisothiazolin-3-one; 2-n-octylbenzisothiazolin-3-one; 2-(2-ethylhexyl)benzisothiazolin-3-one; 2-(2-ethylbutyl)benziothazolin-3-one; 2-(2-phenylethyl) benzisothiazolin-3-one; 2-methylbenzisothiazolin-3-one, 2-octyllsothiazolin-3-one, 4,5-dichloro-2octylisothiazolin-3-one; thiazole derivatives such as 2-(thiocyanomethylthio)-benzthiazole and mercaptobenzthiazole; nitro compounds such as tris(hydroxymethyl)nitromethane; 5bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl, formaldehyde and glyoxal; amides such as chloracetamide; N,N-bis(hydroxymethyl)chloracetamide; N-hydroxymethyl-chloracetamide and dithio-2,2-bis (benzmethyl amide); guanidine derivatives such as 1,6-hexamethylene-bis [5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine, 6-chloro-2,4-diethyl-amino-s-triazine and 4cyclopropylamino-2-methylthio-6-t-butylamino-s-triazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic add and 4-hydroxybenzoic acid and their salts and esters; phenol and derivatives thereof such as 5 chloro-2-(2,4-dichloro-phenoxy)phenol; thio-bis(4-chlorophenol) and 2-phenylphenol; sulphone derivatives such as diiodomethyl-paratolyl sulphone; 2,3,5,6-tetrachloro-4-(methylsulphonyl)pyridine and hexachlorodimethyl sulphone; thioamides such as dimethyldithiocarbamate and its metal complexes, ethylenebisdithiocarbamate and its metal complexes, 2-mercaptopyridine-N-oxide and its metal complexes, azoles such as hexaconazole, propiconazole, azoconazole, cypropconazole; the compounds of Formula (1) in EP 382 375, especially azoxystrobin and chlorphthalonll.

According to a fourth aspect of the present invention there is provided a method for detecting The Polymer comprising the steps:

(a) subjecting a sample containing The Polymer to a detection means whereby the presence of the chromophoric marker in The Polymer generates a detection signal; and optionally (b) calculating the concentration of The Polymer from the detection signal generated in step (a).

Preferably the detection means comprises fluorescence spectrometry or Raman spectrometry.

Preferably the concentration of The Polymer is calculated by translating the intensity of the detection signal in step (a) into the corresponding concentration of The Polymer. The intensity of the detection signal generated will be dependant upon a number of factors including the type and configuration of the detection means and the volume of the sample used. However, irrespective of these factors the signal intensity will be proportional to the concentration of The Polymer present thus enabling calibration of the detection system using standard techniques in the art. For example using a set of calibration standards containing known concentrations of The Polymer.

In a first preferred embodiment of the present method the chromophoric marker comprises a phosphorescent or more preferably a fluorescent group and the detection means is a fluorescence spectrometer comprising:

(i) a means for irradiating the sample containing The Polymer whereby the. chromophoric marker is stimulated from a lower energy level to an excited state;

(ii) a means for detecting radiation (preferably fluorescent radiation) emitted by the chromophoric marker when the marker spontaneously returns to a lower energy level; and (iii) a means for generating a detection signal upon detection of the emitted radiation.

Preferably the means for irradiating the sample containing The Polymer comprises a source of electromagnetic radiation which emits at wavelengths within the absorbtion band of the chromophoric marker. Suitable irradiation means include a laser with a peak wavelength which is within the main absorbtion band of the chromophoric marker. Alternatively a broad-band light source may be used, optionally in conjunction with suitable optical filters to remove undesirable wavelengths outside the absorbtion band of the chromophoric marker.

The preferred means generating a detection signal is a photodetector, for example a silicon photodiode or a charge coupled array. Preferably the photodetector is used in combination with a suitable optical filter which has a transmission band corresponding with the emission band of the chromophoric marker. This minimises the effect of stray light (for example from the irradiating means) on the photodetector, thereby increasing the detection sensitivity. Upon detection of fluorescent radiation from the chromophoric marker the photodetector generates a voltage which is proportional to the intensity of fluorescent radiation generated by the sample. The intensity of fluorescent radiation is proportional to the concentration of the chromophoric marker present in the sample. Accordingly, the concentration of The Polymer can be calculated based upon the magnitude of the voltage signal generated by the photodetector.

In a second preferred embodiment of the present method the detection means comprises a Raman spectrometer.

When monochromatic light irradiates a sample most of the light is scattered elastically with no interaction. However, a small fraction of the incident light interacts with the sample causing fluorescence and inelastic scattering known as the Raman effect. The inelastically scattered radiation contains bands characteristic of the material being irradiated and is called the Raman spectrum.

The Raman effect is very weak and is often swamped by the fluorescence effect. However, the Raman spectrum can be greatly enhanced by tuning the wavelength of the incident radiation to a chromophore in a molecule. This is called Resonance Raman (RR). The strength of the spectrum can also be greatly increased by examining a molecule on a specific silver surface. This is known as Surface Enhanced Raman Spectroscopy (SERS).

The combining of Resonance Raman with SERS gives an increase in detection, sensitivity. This combined effect is called Surface Enhanced Resonance Raman Spectroscopy (SERRS). Another advantage of SERRS is that fluorescence is greatly reduced or quenched and therefore masking of the Raman Spectrum caused by fluorescence is reduced. To perform SERRS the sample of interest is mixed with a silver colloid, irradiated with a monochromatic light and the SERRS spectrum measured. The spectrum is very characteristic of the chromophore of the material examined and the strength is dependent on the concentration of material present.

Thus, in the present method the concentration of The Polymer in the sample is determined by measuring the Raman spectrum generated by the chromophoric marker and the intensity thereof, preferably using the SERRS method as hereinbefore described. The concentration of The Polymer is then determined from the intensity of the spectrum.

An example of a suitable Raman spectrometer is disclosed in U.S. Pat. No. 5,751,415 which is incorporated herein by reference thereto.

According to a fifth aspect of the present invention there is provided a method for maintaining the concentration of The Polymer according to the first aspect of the invention in a medium at or above a target concentration comprising the steps:

(a) measuring the concentration of The Polymer in the medium using the method according to the fourth aspect of the present invention;

(b) comparing the measured concentration with the target concentration; and (c) adding a sufficient quantity of further antimicrobial polymer to the medium to maintain the concentration of The Polymer in the medium at or above the target concentration.

The medium In this aspect of the invention is preferably an aqueous medium, more preferably water from a swimming pool. The preferred methods for measuring the concentration of The Polymer in step (a) are the preferred methods hereinbefore described in relation to the fourth aspect of the present invention, and especially a method which uses fluorescence spectrometry to detect the chromophoric marker in The Polymer.

The target concentration in the present method is preferably the minimum concentration of The Polymer required to prevent antimicrobial growth in the medium. Accordingly, when The Polymer is a polymeric biguanide the target concentration will typically be from 5 to 30 ppm.

Preferably steps (a) to (c) of the present process are automated such that the concentration of The Polymer present in the medium is automatically maintained at or above the target level. Automation is particularly useful for the protection of swimming pools because the concentration of antimicrobial materials in swimming pools can change quickly, for example through contamination of the swimming pool, or by dilution with fresh water.

When the present method is automated it is preferred that step (b) generates an alarm signal when the concentration measured in step (a) falls to or below the target concentration. The alarm signal is then used to activate step (c) of the method and thereby increase the concentration of The Polymer. Preferably the additional antimicrobial polymer in step (c) is added to the medium from a reservoir containing The Polymer.

It is preferred that the concentration of The Polymer in step (a) is constantly monitored because this enables any reduction in concentration below the target level to be quickly detected and thereby reduces the possibility of contamination of the medium through proliferation of micro-organisms in the medium.

The invention is further illustrated by the following examples in which all parts are by weight unless otherwise indicated.

Marker 1

Preparation of Chromophoric Marker N-(6-aminohexyl)-4-(6-aminohexylamino)-1,8-naphthalimide

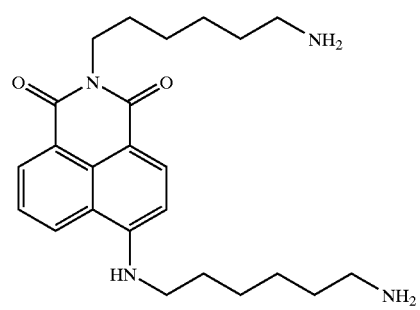

Marker 1

Marker 1 was prepared as follows:

Stage (a) Preparation of N-acetylhexylendiamine

Hexamethylenediamine (90.64 g; 0.6 mol) and acetamide (11.81 g; 0.2 Mol) were stirred and refluxed for 10 hours under nitrogen. The solution was cooled overnight and then distilled under vacuum <100° C. as fast as possible. The N-acetylhexylenediamine was then separated from the resultant mixture by flash chromatography [SiO$_2$/EtOH:25%aq.NH$_3$ (4:1)]. The title product was obtained as a white crystalline product (18.43 g; 58% theory).

Stage (b): Preparation of N-(N-acetyl-6-aminohexyl)-4-(N-acetyl-aminohexylamino)-1,8-naphthalimide 4-Bromo-1,8-naphthalic anhydride (2.77 g; 0.01 mol) and N-acetylhexylendiamine (1.61 g; 1.5 10$^{-3}$mol) were melted together and stirred for 1 hour until the mixture became a brown solid. The compound obtained was purified by chromatography [silica gel/hexane, CH$_2$Cl$_2$ then CH$_2$Cl$_2$:MeOH (10:1; 5:1; 3:1)].

Stage (c): Preparation of N-(6-aminohexyl)-4-(6-aminohexylamino)-1,8-naphthalimide Hydrochloric acid (250 mL; 4 M) was added to the product of stage (b) and the mixture was refluxed for 9 hours. The solution was cooled and neutralised with sodium carbonate. Most of the salt was precipitated with ethanol (2L), the solution filtered and the solvent evaporated. The resulting mixture was salt and a brown oil. Water (100 mL) was added and the product precipitated. The product was extracted into CH$_2$Cl$_2$ (addition of a small amount of MeOH helped dissolved the product in the CH$_2$Cl$_2$ layer), dried over MgSO4 and evaporated to give Marker 1 as an orange solid (1.90 g; 46% theory). mp: 113.6–114.9° C. Marker 1 had the following NMR spectrum:

NMR $^1$H (300 mHz, CDCl$_3$) $\delta_H$: 1.1–1.6 (16H, m, 4×CH$_2$+4×NH$_2$), 1.7–1.9 (4H, m, 4×CH$_2$), 2.7 (4H, m, 2×CH$_2$—NH$_2$), 3.4 (2H, q, Ar—N—CH$_2$). 4.2 (2H, t, >N—CH$_2$), 5.3 (1H, t, Ar—NH—R), 6.7 (1H, d, ArH), 7.6 (1H, t, ArH), 8.1 (1H, d, ArH), 8.4 (1H, d, ArH), 8.5 (1H, d, ArH) ppm m/z (ES-): 409 [M–H]$^-$(100%), 204 [M-2H]$^{2-}$ (15) m/z (ES+): 411 [M+H]$^+$(90%), 227 (100)

Marker 2

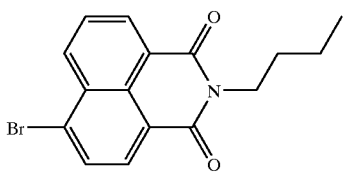

Marker 2

A mixture of 4-bromo-1,8-naphthalic anhydride (2.9 g) and n-butylamine (0.8 g) in ethanol (50 ml) was stirred under reflux for 4 hours. The mixture was filtered. The residue was washed with ether and the ether solution evaporated under reduced pressure to give the title product as white solid (1.1 g).

NMR $^1$H (300 MHz, CDCl$_3$) $\delta_H$: 1.0 (3H, t), 1.4 (2H, m), 1.7 (2H, m), 4.15 (2H, t), 7.85 (1H, t), 8.05 (1 H, d), 8.4 (1H, d), 8.55 (1H, d), 8.7 (1H) ppm Marker 3

Marker 3

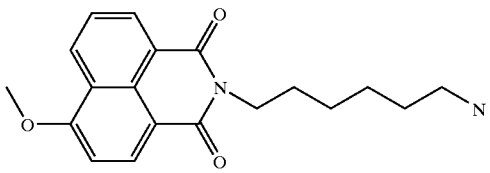

Stage 1: Coupling of Hexamethylenediamine With Wana Resin

Carbonyldiimidazole (12.15 g) was dissolved in dichloromethane (100 ml) and the solution added to Wang resin (5 g of 5 mmol.g-1 material) under nitrogen. The mixture was stirred at room temperature for 6 hours then allowed to stand overnight. After filtering and washing well with dichloromethane a solution of hexamethylenediamine (8.7 g) in dichloromethane (50 ml) was added and the mixture stirred at room temperature for 4 hours. The resin was filtered and washed well with dichloromethane. The product was air dried.

Stage 2

A mixture of the Wang resin derivative (1 g) prepared in stage 1 and 4-bromo-1,8-naphthalic anhydride (1.66 g) in tetrahydrofuran was stirred under reflux overnight then was cooled to room temperature. The resin was filtered, washed with tetrahydrofuran then with dichloromethane then used in the next stage.

Stage 3

The product of stage 2 was stirred with a solution of trifluoroacetic acid (5 ml) in dichloromethane (50 ml) at room temperature for 2 hours. The mixture was filtered and washed well with dichloromethane. The combined filtrates were evaporated under reduced pressure and the resultant residue stirred with ether, filtered and air dried (0.52 g).

Stage 4

A solution of sodium methoxide (0.135 g) in methanol (20 ml) was added to the above product and the mixture stirred under reflux overnight. After cooling to room temperature water was added and the mixture extracted with dichloromethane. The extract was washed with water, dried over magnesium sulphate and was evaporated under reduced pressure (0.2 g).

Marker 4

Marker 4

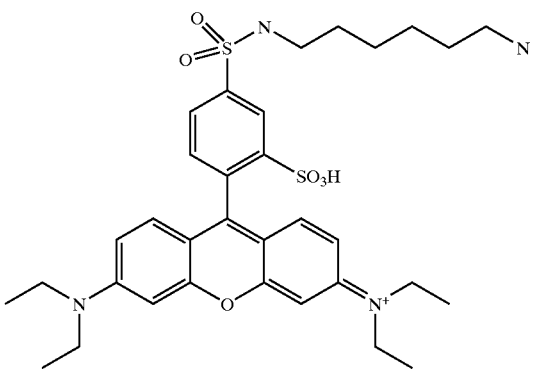

Stage 1

The Wang resin derivative described in stage 1 of the preparation of Marker 3 (0.33 g) was suspended in dichloromethane(20 ml) and triethylamine (0.1 g) added, followed by Sulforhodamine B acid chloride (0.6 g). The mixture was stirred at room temperature for 4 hours, then filtered and washed with dichloromethane.

Stage 2

The above resin was stirred with a 10% solution of trifluoroacetic acid in dichloromethane (30 ml) for 1 hour. Methanol was added to help dissolve the product and the mixture was filtered. The residue was washed with a mixture of dichloromethane and methanol and the combined filtrates were evaporated to dryness to give the title product, a dark red solid (0.3 g).

Marker 5

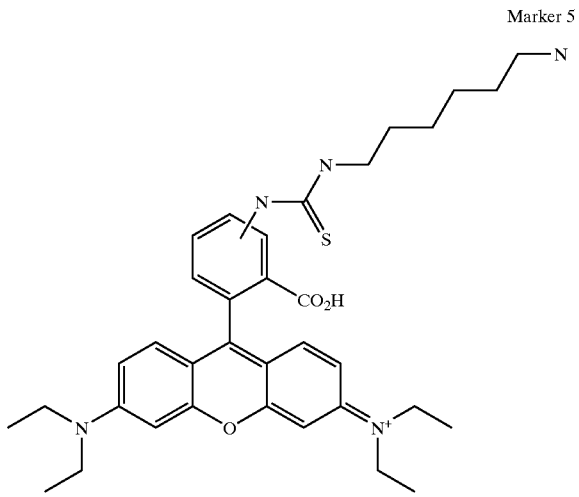
Marker 5

Stage 1

The Wang resin derivative described in stage 1 of the preparation of Marker 3 (0.12 g) was suspended in dichloromethane (10 ml) and Rhodamine B isothiocyanate (200 mg) added. The mixture was stirred at room temperature for 4 hours, then filtered and washed with dichloromethane.

Stage 2

The above resin was stirred with a 10% solution of trifluoroacetic acid in dichloromethane (20 ml) for 1 hour. Methanol was added to help dissolve the product and the mixture was filtered. The residue was washed with a mixture of dichloromethane and methanol and the combined filtrates were evaporated to dryness to give a dark red solid (0.1 g).

EXAMPLE 1

Co-polymer Containing Marker 1 as an In-Chain Group

Hexamethylenediamine dihydrochloride (1.48 g; $8\times10^{-3}$ mol), 2% aqueous ammonium chloride solution (0.5 ml), HMBDA (2 g; $8\times10^{-3}$ mol) and Marker 1 ($3.48\times10^{-3}$ g) were added to a boiling tube. The mixture was then heated at 160° C. for 2 hours. The resulting product was then dissolved in water (4 ml) to stop the co-polymerisation, and the temperature reduced to 70° C. More water (4 ml) and Celite filter aid (0.3 g) were added. The mixture was filtered and the volume made up to 15 mL to give the title product as a 20% aqueous solution.

EXAMPLES 2 TO 4 AND COMPARATIVE EXAMPLE A

Further antimicrobial polymers containing Marker 1 were prepared using the method described in Example 1, except the quantity of Marker 1 used in the co-polymerisation is as shown in Table 1. The number average molecular weight of the resulting copolymer (Mn) was measured using gel permeation chromatography. The polymer of Comparative Example A did not contain Marker 1.

TABLE 1

| Example | % weight of Marker 1 (vs. Total weight) | Mass of Marker 1 (g) | Mn |
|---|---|---|---|
| 1 | 0.1 | $3.48\ 10^{-3}$ | 931.2 |
| 2 | 0.5 | $6.96\ 10^{-3}$ | 841.4 |
| 3 | 1 | $3.48\ 10^{-2}$ | 913.7 |
| 4 | 5 | $6.98\ 10^{-2}$ | 843.0 |
| Comparative Example A | 0 | 0 | 878.3 |

EXAMPLE 5

Co-polymer Containing Marker 1 Prepared in-situ

A mixture of hexamethylenediamine dihydrochloride (14.68 g), HMBDA (20.05 g), ammonium chloride (1.07 g), 4-bromo-1,8-naphthalic anhydride (0.03 g) and water (4 ml) was heated at 160° C. for 2 hours. Water (80 ml) was added and the mixture stirred at 70° C. for 1 hour. Celite filter aid was added, the solution filtered, and the volume adjusted to 150 ml with water to give a 20% solution.

EXAMPLES 6 TO 9 AND COMPARATIVE EXAMPLE B

PHMB polymers containing Markers 2 to 5 were prepared by a method similar to that described in Example 1 except in place of Marker 1 there was used the marker shown in Table 2:

TABLE 2

| Example | Marker | % weight of marker | Mn |
|---|---|---|---|
| 6 | 2 | 0.1 | 1160 |
| 7 | 3 | 0.1 | 1190 |
| 8 | 4 | 0.1 | 1160 |
| 9 | 5 | 0.1 | 1200 |
| Comparative example B | none | 0 | 1190 |

EXAMPLE 10

Anti-Microbial Effect

The Minimum Inhibitory Concentration (MIC) against a range of fungi and bacteria were determined for each of the antimicrobial copolymers prepared in Examples 1 to 4 and Comparative Example A. The MIC results are shown in Table 3:

TABLE 3

| | Fungi | Bacteria | | | | | | |
|---|---|---|---|---|---|---|---|---|
| Example | Ca | Pp | Bs | Ec | Psa | Sa | Ps.fl | K.pn |
| 1 | 62.5 | 32 | 0.25 | 0.25 | 16 | 0.25 | 8 | 1 |
| 2 | 62.5 | 32 | 0.25 | 0.25 | 32 | 0.25 | 8 | i |
| 3 | 32 | 32 | 0.25 | 0.25 | 16 | 0.25 | 8 | 1 |
| 4 | 62.5 | 32 | 0.25 | 0.25 | 16 | 0.25 | 8 | 1 |
| Comparative Example A | 62.5 | 32 | 0.25 | 0.25 | 16 | 0.25 | 8 | 1 |
| Marker 1 | 999 | 999 | 500 | 500 | 999 | 32 | 500 | 999 |

In Table 3 the following abbreviations are used:
Ca  Candida albicans   NCYC 10231
Bs  Bacillus subtilis   NCIB 1650
Ec  Escherichia coli   NCIB 9132

TABLE 3-continued

| | Fungi | | | Bacteria | | | |
|---|---|---|---|---|---|---|---|
| Example | Ca | Pp | Bs | Ec | Psa | Sa | Ps.fl | K.pn |

| | | |
|---|---|---|
| Psa | Pseudomonas aeruginosa | NCIB 10421 |
| Sa | Staphylococcus aureus | NCIB 9518 |
| Pp | Penicillium funiculosum | IMI 114933 |
| Psfl | Pseudomonas fluorescens (with Lux AB gene) | our ref D481 |
| Kpn | Klebsiella pneumoniae | ATCC 4352 |

Table 3 clearly shows that the presence of Marker 1 has no marked effect on the MIC compared to the polymer of Comparative Example A which does not contain Marker 1.

Table 3 also shows that Marker 1 itself has little or no antimicrobial effect compared to the copolymers containing it.

Further tests showed there was no effect on the speed of kill of Examples 1 to 4 containing Marker 1 compared to the poly(hexamethylenebiguanide) itself and which is free of Marker 1.

EXAMPLE 11

Fluorescent Detection

A 20% solution of the antimicrobial polymer prepared in Example 3 (1% of Marker 1) was diluted several times with distilled water to give a range of concentrations of from 1 to $10^{-8}$ gL$^{-1}$ to of the antimicrobial polymer.

The solution containing 1 gL$^{-1}$ of the antimicrobial polymer was analysed by UV/Vis spectroscopy (Perkin-Elmer, Lambda 15, UV/Vis spectrometer). An absorbance peak was found at 456 nm. The same analysis on a solution containing 1 g/L of the polymer of Comparative Example A (no Marker 1 present) showed no peak at this wavelength. Using a fluorescence spectrometer (Perkin-Elmer, LS-5B, luminescence spectrometer), the lambda max, excitation wavelength was found to be 452 nm and the emission spectrum was scanned between 475 and 800 nm. The marker maximum emission was 532 nm. All the solutions were scanned and it was found that the detection limit for this particular peak was for the $10^{-8}$ gL$^{-1}$ solution of The Polymer according to the present invention.

The above procedure was repeated using other antimicrobial polymers described in the previous Examples. The measured maximum excitation and emission wavelengths for each antimicrobial polymer is shown in Table 4.

TABLE 4

| Antimicrobial polymer | Marker present in polymer | Concentration of marker present in polymer (% by wt) | Max. Excitation (nm) | Max. Emission (nm) |
|---|---|---|---|---|
| Example 6 | Marker 2 | 0.1 | 454 | 558 |
| Example 7 | Marker 3 | 0.1 | 383,453 | 455,560 |
| Example 8 | Marker 4 | 0.1 | 565 | 593 |
| Example 9 | Marker 5 | 0.1 | 554 | 584 |

What is claimed is:

1. An antimicrobial polymeric biguanide, said polymeric biguanide carrying a covalently bound chromophoric marker.

2. An antimicrobial polymeric biguanide according to claim 1 wherein said chromophoric marker comprises a chromophoric group which has a major absorption and/or emission band in the range of from 275 to 1500 nm.

3. An antimicrobial polymeric biguanide according to claim 1 wherein the chromophoric group is a fluorescent group.

4. An antimicrobial polymeric biguanide according to claim 1 wherein the chromophoric marker is covalently bound to the antimicrobial polymeric biguanide as a pendant group or a terminal group on the polymer chain, or as an in-chain group in the polymer chain.

5. An antimicrobial polymeric biguanide according to claim 1 wherein the chromophoric marker is present as a terminal or pendant group on the polymer chain.

6. An antimicrobial polymeric biguanide according to claim 5 wherein the antimicrobial polymeric biguanide to which the chromophoric marker is bound is a polymeric biguanide which contains at least one biguanide unit of Formula (3):

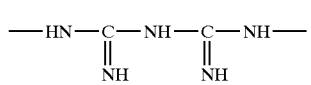

Formula 3

7. An antimicrobial polymeric biguanide according to claim 6 wherein the polymeric biguanide is a linear polymeric biguanide which has a recurring polymeric unit represented by Formula (4):

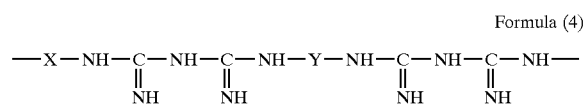

Formula (4)

wherein X and Y may be the same or different and represent bridging groups in which, together, the total number of carbon atoms directly interposed between the pairs of nitrogen atoms linked by X and Y is not greater than 17.

8. An antimicrobial polymeric biguanide according to claim 7 wherein the polymeric biguanide is a mixture of poly(hexamethylenebiguanide) polymer chains in which the individual polymer chains, excluding the terminal groups, are represented by Formula (5) and salts thereof:

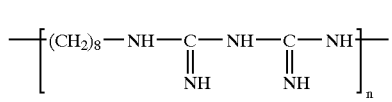

Formula (5)

wherein the value of n is from 4 to 40.

9. An antimicrobial polymeric biguanide according to claim 1 obtainable by co-polymerising a chromophoric marker, a bisdicyandiamide having the formula:

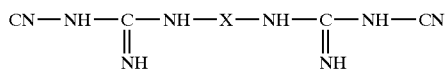

and a diamine $H_2N$—Y—$NH_2$, wherein X and Y may be the same or different and represent bridging groups in which, together, the total number of carbon atoms directly interposed between the pairs of nitrogen atoms linked by X and Y is not less than 9 and not greater than 17.

10. An antimicrobial polymeric biguanide according to claim 9 obtainable by co-polymerising hexamethylenediamine, hexamethylene-1,6-bis dicyandiamide and a chromophoric marker.

11. An antimicrobial polymeric biguanide according to claim 1 wherein the covalent bond between the chromophoric marker and the polymeric biguanide is formed by means of one or more reactive functional group on the chromophoric marker which is capable of forming a covalent bond with the polymeric biguanide and/or monomer precursors used to make the polymeric biguanide.

12. An antimicrobial polymeric biguanide according to claim 11 wherein the chromophoric marker carrying the reactive functional group(s) is of the Formula (1):

$$Ch\text{-}\{[(T)_mL]_nX\}_p \quad \text{Formula (1)}$$

wherein:

| | |
|---|---|
| Ch | is a chromophoric group; |
| L | is a divalent aliphatic linking group; |
| X | is a reactive functional group; |
| T | is —O—, —S—, —NR$^1$—, —NR$^1$C(O)NR$^1$—, —NR$^1$C(S)NR$^1$—, —NR$^1$C(O)—, —OC(O), =N— or —SO$_2$NR$^1$—; |
| R$^1$ | is H, optionally substituted alkyl or optionally substituted phenyl; |
| m and n | independently are 0 or 1; and |
| P | is 1 or 2. |

13. An antimicrobial polymeric biguanide according to claim 12 wherein the chromophoric marker carrying the reactive functional group(s) is of the Formula (2):

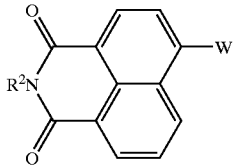

Formula (2)

wherein:
W is —NR$^3$R$^4$, —OR$^5$ or halogen;
R$^2$, R$^3$ and R$^5$ are each, independently, alkyl optionally substituted by a reactive functional group;
R$^4$ is H or alkyl optionally substituted by a reactive functional group;
provided that at least one of R$^2$ R$^3$ R$^4$ or R$^5$ is substituted by a reactive functional group.

14. An antimicrobial polymeric biguanide according to claim 13 wherein the chromophoric marker carrying the reactive functional group(s) is N-(6-aminohexyl)-4-(6-aminohexylamino)-1,8-naphthalimide, N-(6-aminohexyl)-4-methoxy-1,8-naphthalimide, N-(6-aminohexyl)-4-bromo-1,8-naphthalimide or N-hexyl-4-(6-aminohexyl)-1,8-naphthalimide.

15. An antimicrobial polymeric biguanide according to claim 9 obtainable by co-polymerising hexamethylenediamine, hexamethylene-1,6-bis dicyandiamide and 4-bromo-1,8-naphthalic anhydride.

16. A composition comprising antimicrobial polymers at least one of which is an antimicrobial polymeric biguanide according to claim 1.

17. A composition comprising a carrier and an antimicrobial polymeric biguanide according to claim 1.

18. A method for inhibiting microbiological growth on, or in, a medium which comprises treating the medium with an antimicrobial polymer according to claim 1.

19. A method for detecting an antimicrobial polymeric biguanide according to claim 1 on or in a medium comprising:

(a) subjecting a sample of the medium containing said antimicrobial polymer polymeric biguanide to a detection means whereby the presence of the chromophoric marker in the antimicrobial polymer generates a detection signal; and optionally (b) calculating the concentration of the antimicrobial polymeric biguanide from the detection signal generated in step (a).

20. A method according to claim 19 wherein the detection means comprises flourescence spectrometry, Raman spectrometry or surface enhanced resonance Raman spectrometry.

21. A method for maintaining the concentration of an antimicrobial polymeric biguanide carrying a covalently bound chromophoric marker in a medium at or above a target concentration comprising:

(a) measuring the concentration of the antimicrobial polymer in the medium using the method according to claim 19;

(b) comparing the measured concentration with the target concentration; and (c) adding a sufficient quantity of further antimicrobial polymeric biguanide to the medium to maintain the concentration of the antimicrobial polymeric biguanide in the medium at or above the target concentration.

22. A composition comprising a carrier and a composition according to claim 16.

23. A method for inhibiting microbiological growth, on, or in a medium which comprises treating the medium with a composition according to claim 16.

* * * * *